US00PP29115P3

(12) United States Plant Patent
Park

(10) Patent No.: US PP29,115 P3
(45) Date of Patent: Mar. 13, 2018

(54) ***COREOPSIS* PLANT NAMED 'URITW02'**

(50) Latin Name: ***Coreopsis rosea*×*Coreopsis verticillata***
Varietal Denomination: URITW02

(71) Applicant: Uriseed Institute, Icheon-si (KR)

(72) Inventor: Kong Young Park, Icheon-si (KR)

(73) Assignee: URISEED INSTITUTE, Icheon-si (KR)

( * ) Notice: Subject to any disclaimer, the term of this patent is extended or adjusted under 35 U.S.C. 154(b) by 32 days.

(21) Appl. No.: 14/999,136

(22) Filed: Mar. 31, 2016

(65) Prior Publication Data

US 2017/0049030 P1 Feb. 16, 2017

(30) Foreign Application Priority Data

Aug. 14, 2015 (QZ) ..... PBR 20151906

(51) Int. Cl.
*A01H 5/02* (2006.01)

(52) U.S. Cl.
USPC ..... Plt./417

(58) Field of Classification Search
USPC ..... Plt./417
CPC ..... A01H 5/025; A01H 5/02; A01H 5/00
See application file for complete search history.

(56) References Cited

PUBLICATIONS

Horticulture Week Plantarium 2015 new plants announced, retrieved on Jun. 26, 2017, retrieved from the Internet at <http://www.hortweek.com/plantarium-2015-new-plants-announced/ornamentals/article/1359559> pp. 1 and 7.*

New Plants and Flower Three Korean *Coreopsis* varieties launched in Europe, retrieved on Jun. 26, 2017, retrieved from the Internet at <http://www.newplantsandflowers.com/three-korean-coreopsis-varieties-launched-in-europe/> 2 pp.*

* cited by examiner

*Primary Examiner* — June Hwu
(74) *Attorney, Agent, or Firm* — Penny J. Aguirre

(57) ABSTRACT

A new cultivar of hybrid *Coreopsis* plant named, 'URITW02', that is characterized by its small inflorescences with ray florets that are that are pink in color, its dwarf plant habit, and its involucral bracts that are small in size and oblong to ovate in shape.

2 Drawing Sheets

Botanical classification: *Coreopsis rosea*×*Coreopsis verticillata.*

Variety denomination: 'URITW02'.

CROSS REFERENCE TO RELATED APPLICATIONS

This application is co-pending with U.S. Plant Patent Applications filed for plants derived from the same breeding program that are entitled *Coreopsis* Plant Named 'URITW01' (U.S. Plant patent application Ser. No. 14/999,128) and *Coreopsis* Plant Named 'URITW03' (U.S. Plant patent application Ser. No. 14/999,135).

BACKGROUND OF THE INVENTION

The present invention relates to a new and distinct cultivar of *Coreopsis* plant, botanically of hybrid origin and known as *Coreopsis* 'URITW02' and will be referred to hereinafter by its cultivar name, 'URITW02'. The new cultivar of *Coreopsis* is an herbaceous perennial grown for landscape and container use.

The new invention arose from an ongoing controlled breeding program in Icheon-si, Korea. The objective of the breeding program is to develop hybrid cultivars of *Coreopsis* with unique flower colors and dwarf plant habit.

The new cultivar arose as a mutation using gamma radiation of un-rooted cuttings of 'URITW01' in January of 2011. 'URITW02' was selected in September 2011 as a single unique plant amongst the resulting seedlings.

Asexual propagation of the new cultivar was first accomplished by stem cuttings by the Inventor in Icheon-si, Korea in September of 2011. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'URITW02' as unique cultivar of *Coreopsis.*

1. 'URITW02' exhibits small inflorescences with ray florets that are that are pink in color.
2. 'URITW02' exhibits a dwarf plant habit.
3. 'URITW02' exhibits involucral bracts that are small in size and oblong to ovate in shape.

The parent plant of 'URITW02', 'URITW01', differs from 'URITW02' in having inflorescences with ray florets that are crimson red in color. 'URITW02' can be compared to the *Coreopsis* cultivars 'Limerock Ruby' (U.S. Plant Pat. No. 15,455) and 'URITW03'. 'Limerock Ruby' differs from 'URITW02' in having a plant height that is 50% taller, in having a wider plant spread, and in having inflorescences that are larger in size with ray florets that are crimson red in color. 'URITW03' differs from 'URITW02' in having inflorescences with ray florets that are light red in color.

BRIEF DESCRIPTION OF THE DRAWINGS

The accompanying colored photographs illustrate the overall appearance and distinct characteristics of the new *Coreopsis*. The photographs were taken of a 3 month-old plant of 'URITW02' as grown outdoors in a 13-cm container in Boskoop, The Netherlands.

The photograph in FIG. 1 provides a side view of a plant of 'URITW02' in bloom.

Figure 1:
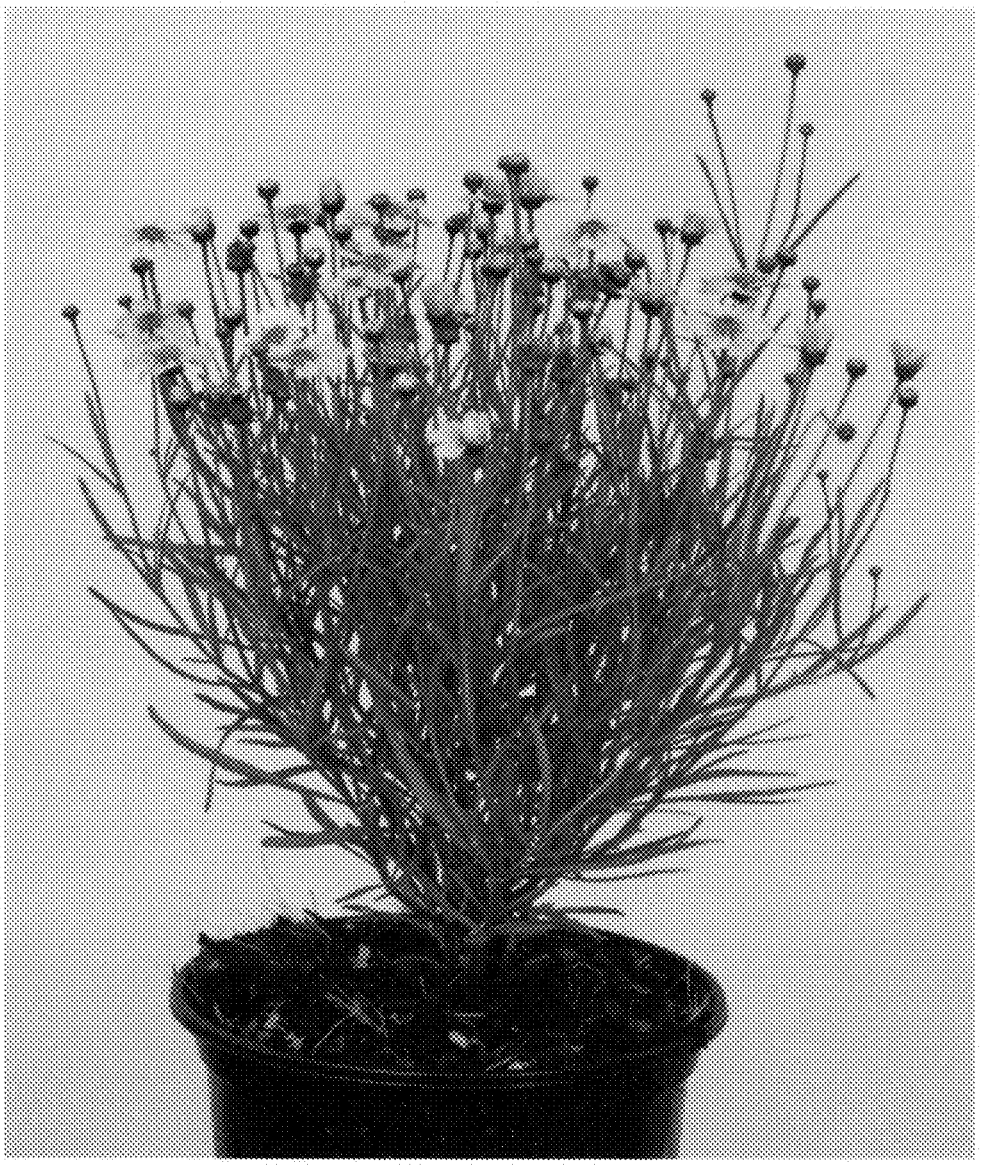
Figure 2:
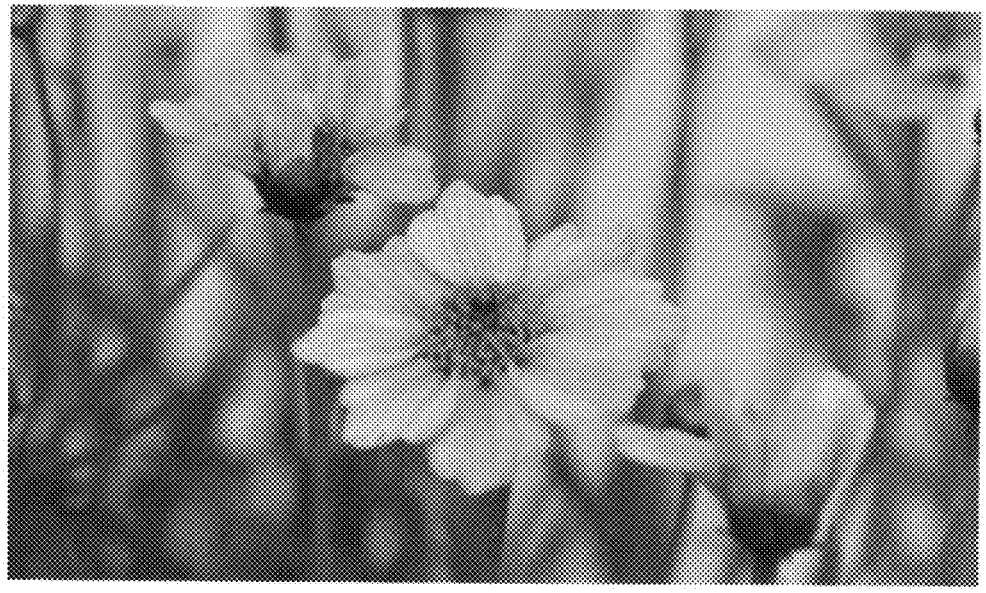

The photograph in FIG. 2 provides a close-up view of an inflorescence of 'URITW02'.

Figure 3:
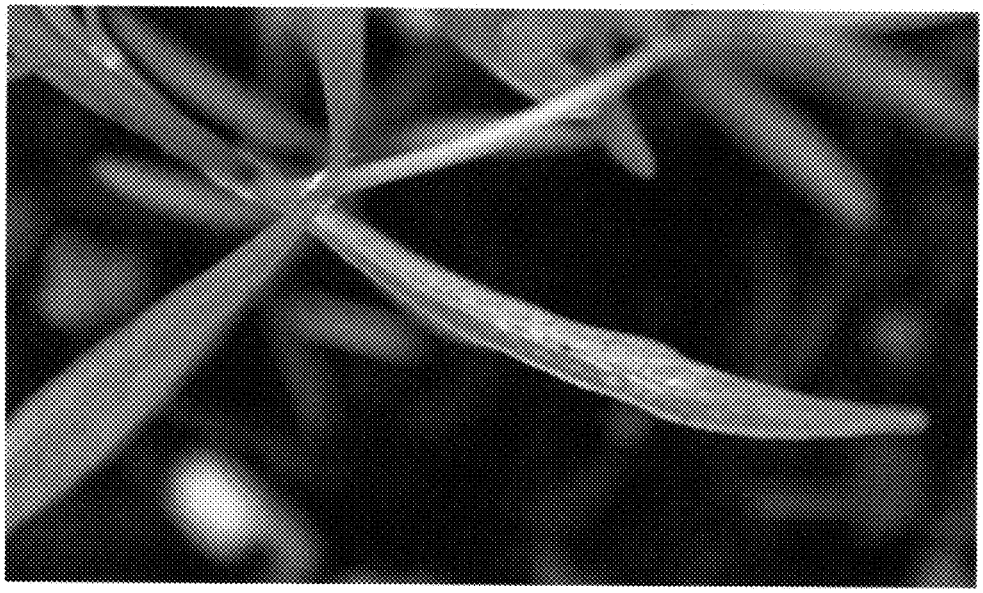

The photograph in FIG. 3 provides a close-up view of the foliage of 'URITW02'.

The colors in the photograph may differ slightly from the color values cited in the detailed botanical description, which accurately describe the colors of the new *Coreopsis*.

DETAILED BOTANICAL DESCRIPTION

The following is a detailed description of 3 month-old plants of the new cultivar as grown outdoors in 13-cm containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Early summer to late summer in The Netherlands.

*Plant type*.—Herbaceous perennial.

*Plant habit*.—Dwarf and upright.

*Height and spread*.—An average of 22.4 cm in height and 21.0 cm in width.

*Cold hardiness*.—At least to U.S.D.A Zone 4.

*Diseases and pests*.—No susceptibility or resistance to diseases or pests has been observed.

*Root description*.—Fibrous when young, becoming fleshy with age, 162D in color.

*Propagation*.—Stem cuttings.

*Root development*.—An average of 10 days for root initiation and about 5 weeks to produce a young rooted plant in a 10-cm container.

*Growth rate*.—Moderate.

Stem description:

*Shape*.—Rounded.

*Stem color*.—144A.

*Stem size*.—An average of 7.2 cm in length (excluding inflorescence) and 1.5 mm in diameter.

*Stem surface*.—Glabrous and glossy.

*Stem aspect*.—Upward and moderately outward.

*Stem strength*.—Strong.

*Branching habit*.—Well-branched, an average of 27 lateral branches.

*Internode length*.—An average of 2.7 cm.

Foliage description:

*Leaf division*.—Simple.

*Leaf margins*.—Entire.

*Leaf size*.—An average of 4.5 cm in length and 3.5 mm in width.

*Leaf shape*.—Narrow lanceolate.

*Leaf base*.—Narrow cuneate.

*Leaf apex*.—Acute.

*Leaf venation*.—Pinnate, color; upper surface 143A and lower surface 144A.

*Leaf attachment*.—Sessile.

*Leaf arrangement*.—Opposite.

*Leaf surface*.—Both surfaces dull and glabrous.

*Leaf color*.—Young and mature upper surface; 143A, young and mature lower surface; 143B.

*Leaf number*.—An average of 6 leaves (3 pairs) per stem.

Inflorescence description:

*Inflorescence type*.—Terminal capitulate, with a single row of ray florets surrounding disk florets in the center.

*Lastingness of inflorescence*.—An average of 3 weeks, self-cleaning.

*Fragrance*.—Moderate to faint, of musk and straw.

*Quantity of inflorescences*.—An average of 1 per lateral branch.

*Inflorescence size*.—An average of 2.1 cm in diameter and 7 mm in height, disk portion an average of 6 mm in diameter.

*Inflorescence buds*.—An average of 4 mm in depth and in diameter, globular in shape, color; 146A with apex 152C to 152D.

*Peduncle*.—Primary; an average of 7.2 cm in length and 1 mm in width, held straight upright, secondary; an average of 4.8 cm in length and 1 mm in width, held at an average angle of 30° to primary peduncle, slightly glossy and glabrous on all surfaces, 144B in color and moderately strong.

Involucral bracts:

*Bract number*.—Two rows, an average of 8 (inner row) and 6 (outer row).

*Bract arrangement*.—Rotate, placed in two separate rows.

*Bract size*.—Outer bracts; an average of 2 mm in length and 1.5 mm in width, inner bracts; an average of 5 mm in length and 3 mm in width.

*Bract color*.—Inner bracts; 12A heavily suffused with N25C with base 146A and outer bracts; 143A.

*Bract texture*.—Glabrous and dull on upper and lower surfaces of outer and inner bracts.

*Bract apex*.—Outer bracts; obtuse and inner bracts; acute.

*Bract base*.—Broadly cuneate on inner and outer bracts.

*Bract margins*.—Entire.

*Bract shape*.—Outer bracts; ovate to oblong, inner bracts; ovate.

Ray florets (sterile):

*Number*.—An average of 8 arranged primarily in one row.

*Shape*.—Obovate.

*Size*.—An average of 1 cm in length and 7 mm in width.

*Apex*.—Irregularly lobed with an average of 3 acute lobes, lobes are bluntly acute and center lobe is about 1.5 mm longer than the lateral lobes.

*Base*.—Rounded.

*Margins*.—Entire with apex lobed.

*Aspect*.—Held horizontal.

*Texture*.—Glabrous and dull on both surfaces, inner surface is slightly velvety and outer surface is slightly carinate.

*Color*.—Upper surface when opening; 70C, lower surface when opening; 179D, upper and lower surface when fully open; 70C with veins 70B, color not fading.

Disc florets (perfect):

*Shape*.—Tubular, spirally arranged on disc.

*Apex*.—Acute

*Base*.—Lower 75% fused into tube.

*Number*.—About 50.

*Size*.—An average of 4.5 mm in length and 1 mm in width at the apex and 0.4 mm in width at the base.

*Color*.—En masse; 169D, corolla; 177A with base of tube 5B in color, flared portion is 169D.

*Receptacle*.—An average of 1 mm in diameter and depth, 144B in color.

Reproductive organs:

*Presence*.—Disc florets are perfect, ray flowers are sterile.

*Gynoecium*.—1 pistil, an average of 2 mm in length, style; an average of 1.5 mm in length and 16A in color, stigma is decurrent and 21A to 21B in color, ovary is 150D in color.

*Androecium*.—5 stamens, anther; basifixed and linear in shape, an average of 1 mm in length and 203D in color, pollen is low in quantity and 17B in color.

*Fruit/seed*.—No fruit or seed development was observed to date.

It is claimed:

1. A new and distinct cultivar of *Coreopsis* plant named 'URITW02' as herein illustrated and described.

* * * * *